(12) United States Patent
Park et al.

(10) Patent No.: US 9,304,106 B1
(45) Date of Patent: Apr. 5, 2016

(54) HIGH DUTY CYCLE TRAPPING ION MOBILITY SPECTROMETER

(71) Applicant: Bruker Daltonik GmbH, Bremen (DE)

(72) Inventors: Melvin Andrew Park, Billerica, MA (US); Oliver Räther, Lilienthal (DE)

(*) Notice: Subject to any disclaimer, the term of this patent is extended or adjusted under 35 U.S.C. 154(b) by 0 days.

(21) Appl. No.: 14/614,463

(22) Filed: Feb. 5, 2015

(51) Int. Cl.
*H01J 49/26* (2006.01)
*H01J 49/36* (2006.01)
*G01N 27/62* (2006.01)
*H01J 49/42* (2006.01)

(52) U.S. Cl.
CPC .............. *G01N 27/624* (2013.01); *H01J 49/36* (2013.01); *H01J 49/4225* (2013.01)

(58) Field of Classification Search
USPC .............. 250/281, 282, 283, 288, 289, 526
See application file for complete search history.

(56) References Cited

U.S. PATENT DOCUMENTS

| | | | | |
|---|---|---|---|---|
| 5,789,745 A * | 8/1998 | Martin | ................ | H01J 49/0018 250/281 |
| 7,838,826 B1 * | 11/2010 | Park | ..................... | G01N 27/622 250/281 |
| 8,288,717 B2 * | 10/2012 | Park | ..................... | G01N 27/622 250/281 |
| 8,766,176 B2 * | 7/2014 | Park | ..................... | G01N 27/626 250/281 |
| 8,809,769 B2 * | 8/2014 | Park | ..................... | G01N 27/622 250/281 |
| 8,941,054 B2 * | 1/2015 | Park | ..................... | G01N 27/624 250/282 |
| 8,941,055 B2 * | 1/2015 | Park | ..................... | G01N 27/622 250/282 |
| 2009/0134321 A1 * | 5/2009 | Hoyes | ..................... | C08L 23/04 250/282 |

* cited by examiner

*Primary Examiner* — Bernard E Souw
(74) *Attorney, Agent, or Firm* — Benoit & Cote, Inc.

(57) ABSTRACT

The invention provides a trapping ion mobility analyzer and methods for operating the ion mobility analyzer. The trapping ion mobility analyzer comprises an RF field for radially confining ions along an axis, a region with an axial electric DC field and a gas flow along the axis counteracting the electric DC field in the region, wherein the region either comprises a rising edge with an increasing axial electric DC field or a falling edge with a decreasing axial electric DC field and wherein the slope of the electric field strength along the axis is not constant at a substantial portion of the edge.

20 Claims, 5 Drawing Sheets

HIGH DUTY CYCLE TRAPPING ION MOBILITY SPECTROMETER

BACKGROUND OF THE INVENTION

1. Field of the Invention

The invention relates to devices and methods for the acquisition of mass spectra of ions separated by their mobility.

2. Description of the Related Art

Mass spectrometers can only ever determine the ratio of the ion mass m to the number z of charges of the ion. Where the terms "mass of an ion" or "ion mass" are used below for simplification, they always refer to the mass m of the ion, divided by the dimensionless number z of elementary charges. "Ion species" shall denote ions having the same elemental composition, the same charge and the same three-dimensional structure. The ion species generally comprise all ions of an isotope group, which consist of ions of slightly different masses, but virtually the same mobilities. "Isomers" refer to molecules with the same elemental composition but different spatial arrangements of the elements or groups of elements within the molecule.

Particularly for bioorganic molecules, knowledge about the different kinds of isomers becomes more and more essential: isomers related to the primary structure (structural isomers) and particularly isomers related to the secondary or tertiary structure (conformational isomers). All Isomers have different geometrical forms but exactly the same mass. It is therefore impossible to differentiate between isomers on the basis of their mass. Some information as to the structure can be obtained from fragment ion mass spectra; however, an efficient and certain way to recognize, distinguish, and select such isomers is to separate their ions according to their different mobilities.

The mobility of ions can be measured via their drift velocities in a gas under the influence of an electric field. Either a drift region is filled with an inert gas such as helium, nitrogen or argon at rest, and the ions of the substance under investigation are pulled through the resting gas by means of a (mostly homogeneous) electric field, or the ions are blown by a gas against a spatially increasing electrical field (a "field barrier"), where the ions assume equilibrium positions along the rising field according to their mobility. In a resting gas and under a constant electric field strength E, the drift velocity $v_d$ of ions in the gas is proportional to the electric field strength E: $v_d = K \times E$. The proportionality factor K is called the "ion mobility coefficient" (or simply "ion mobility") of the ion species. The ion mobility K is particularly a function of the collision cross-section of the ions, but influenced by the gas temperature, gas pressure, gas speed, type of gas, and ion charge.

A number of academic research groups have coupled ion mobility spectrometers that use long drift tubes with mass spectrometers. A pressure range of several hectopascals has been adopted almost universally for the mobility drift region. For achieving high mobility resolution, drift regions with several meters are necessary, and electric field strengths of 2,000 volts per meter and more are applied. The ions are usually introduced into the drift region in the form of short ion pulses by a gating device, producing spatially small ion clouds, which are pulled through the drift region by the electric field. In the gas of the drift region, these ion clouds are subject to diffusion. The diffusion acts equally in all directions, radially as well as axially, limiting the mobility resolution $R_{mob} = K/\Delta K = v_d/\Delta v_d$, where $\Delta K$ is the width of the ion signal of the mobility K at half height, and $\Delta v_d$ is the correspondent difference in speed. Mobility values above $R_{mob} = 60$ can be regarded as "high resolution mobility". In the best cases, mobility resolutions up to $R_{mob} = 200$ have been achieved in long drift tube instruments.

High-resolution time-of-flight mass spectrometers with orthogonal injection of the ions (OTOF-MS), in particular, have proven successful for combinations of mobility spectrometers with mass spectrometers. For such combinations, the high-resolution ion mobility spectrometers of the current type have the disadvantage of being several meters long. Such a solution is unfavorable for instruments marketed commercially. Even ion mobility spectrometers with a straight drift region offering only moderate resolution are about one meter long. For the construction of small, high-resolution mobility analyzers, one therefore has to look for a solution which shortens the overall length but does not diminish the mobility resolution.

In document U.S. Pat. No. 7,838,826 B1 (M. A. Park, 2008), an ion mobility spectrometer is presented, the length of which amounts to about five centimeters only. It is based upon a moving gas which drives ions against and over an electric counter-field barrier in a special ion tunnel at the exit of a modified ion funnel built into an orthogonal time-of-flight mass spectrometer. Unlike many other trials to build small ion mobility spectrometers, the small device by M. A. Park has already achieved ion mobility resolutions up to $R_{mob} = 250$.

Figure 1:
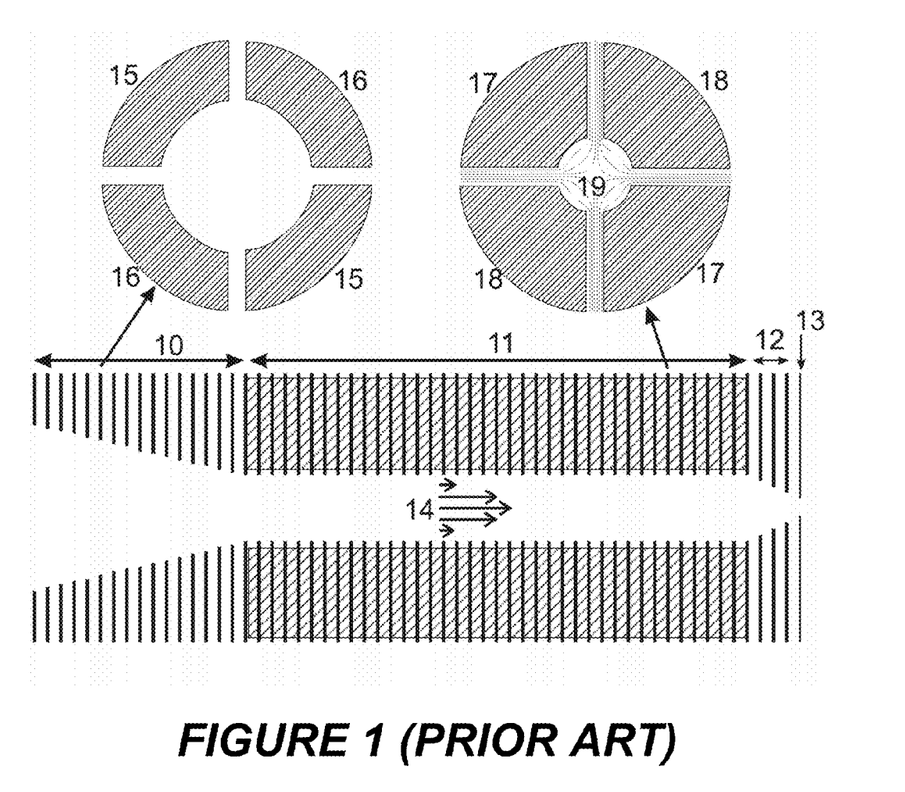
Figure 2:
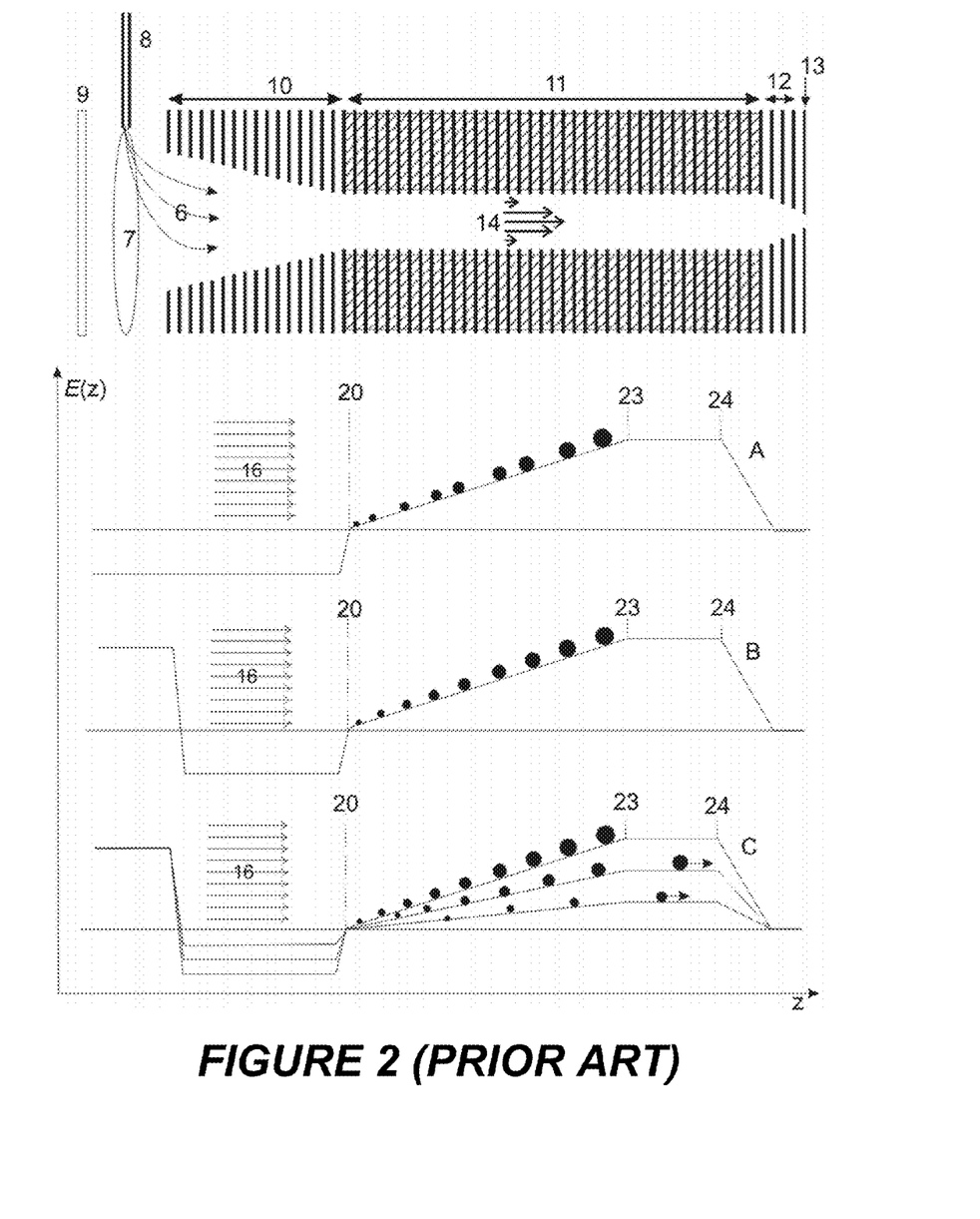

The apparatus of M. A. Park and its operation are schematically illustrated in FIGS. 1 and 2. In the bottom part of FIG. 1, the basic design of the device is presented, with an entrance funnel (10) and an exit funnel (12), both with openings between the electrodes to let escape the gas. Between the two funnels (10, 12), a closed tube-like quadrupole tunnel (11) is formed by thin electrodes and arranged along the z-axis. The electrodes are separated from each other by insulating material closing the gaps between the electrodes forming a circular tube. At the top of FIG. 1, the electrodes (15, 16) of the funnel (10) and the electrodes (17, 18) of the quadrupole tunnel (11) are shown. They are segmented into quadrants to allow for the generation of a quadrupolar RF electric field inside. The electrodes of the tube-like tunnel (11) are shown with equipotential lines of the quadrupolar RF field inside the tube at a given time. The differential pumping system of the mass spectrometer, surrounding the ion mobility spectrometer, is dimensioned to cause a gas to flow through the tube-like tunnel (11) in a laminar way, thereby approximating a parabolic velocity profile (14). Ions entering the first funnel (10) are entrained by the gas and collisionally focused onto the axis of the tube-like tunnel (11) under the effect of the pseudopotential. They move, driven by the gas, along the axis of the tube-like tunnel (11) towards its exit through the apertured diaphragm (13). Most of the gas escapes through gaps between the electrodes of the second funnel (12).

Within the tube-like tunnel (11), an electric DC field barrier stops the ions and spatially separates the ions by their mobilities.

An ion funnel is usually operated with apertured diaphragms the opening of which tapers to smaller diameters thus forming an inner volume in the shape of a funnel. The two phases of an RF voltage are applied alternately to the diaphragms to build up a pseudopotential which keeps the ions away from the funnel walls. A DC potential gradient at the diaphragms drives the ions to and through the narrow end of the funnel. The first (entrance) ion funnel (10) is here built from electrodes which are divided into four parts to allow a more sophisticated RF field.

FIG. 2 outlines the operation of this device. Entrained by a gas (7), ions from an electrospray ion source (not shown) are introduced via capillary (8) into the first chamber of a vacuum system. A repelling DC potential applied to the repeller plate (9) drives the ions (6) into the entrance funnel (10) of the mobility spectrometer. The entrance funnel (10) guides the ions into the tube-like tunnel (11), where the ions are driven by the gas flow (14) against an electric DC field barrier. In the bottom part of FIG. 2, three phases of the profile of the electric DC field barrier are shown. Between z-axis locations (20) and (23), the axial electric field increases linearly, generated by a quadratically increasing electric potential. Between z-axis locations (23) and (24), the field remains substantially constant, forming a plateau of the electric DC field barrier, generated by a linear increase of the electrical potential. In a simple device, the electric field profile can be generated by a single voltage, which is applied to the diaphragm electrode at location (24) and divided by precision resistors along the diaphragm electrodes of the tube-like tunnel (11). The resistors between location (20) and (23) increase linearly, the resistors between (23) and (24) have equal resistivity.

The operation starts with an "ion accumulation phase" (A). By a voltage on the order of 300 volts, the steepest electric field profile is generated, producing the highest electric DC field barrier. The ions are driven by the gas flow, symbolically indicated by the arrows (16), against the electric DC field barrier and are stopped there because they cannot surmount the electric field DC barrier. The ions are accumulated on the rising edge of the electric DC field barrier between locations (20) and (23), where ions of low mobility (mainly heavy ions of large collision cross section) collect in the high field near the upper end of the rising edge, whereas ions of high mobility gather in the low field near the foot of the rising edge, as indicated by the size of the dots symbolizing the ions. In a second phase (B), the "trap phase", the supply of ions is stopped by an attracting voltage at the repeller plate (9), and the ions finally reach their equilibrium locations on the rising edge of the electric DC field barrier. The trap phase is very short in time; the ions assume their equilibrium location in about one millisecond. In a third phase (C), the "scan phase", the supply voltage of the electric DC field barrier is steadily decreased, and ions of increasing mobility can escape towards an ion detector, particularly to a mass spectrometer operating as ion detector.

The measured total ion current curve presents directly the ion mobility spectrum from low ion mobilities to high ion mobilities. The device is denominated "TIMS", "trapped ion mobility spectrometer". Regarding the theoretical basis, see the research article "Fundamentals of Trapped Ion Mobility Spectrometry" (K. Michelmann, J. A. Silveira, M. E. Ridgeway and M. A. Park, J. Am. Soc. Mass Spectrom., January 2015, volume 26, issue 1, pages 14-24).

Improvements of the scan modes for this apparatus have been made to achieve a linear mobility scale, or a constant resolution along the mobility scale (M. A. Park et al., U.S. Pat. No. 8,766,176 B2). Using two of these ion mobility spectrometers in series, mobility filters can be built (M. A. Park et al., US 2012/0273673 A1).

The ion mobility resolution $R_{mob}$ was found mainly to depend on the scan speed (acquisition speed). The higher the scan speed, the lower the resolution. As already mentioned, ion mobilities of $R_{mob}=250$ have been achieved with the small apparatus at slow scans. Since ions generated in the ion source are lost during the scan phases, the utilization rate of ions produced in an ion source, accumulated, and subsequently analyzed in an analyzer, is determined by the ratio $q=t_a/(t_a+t_s)$ wherein $t_a$ is the ion accumulation time and $t_s$ the measuring scan time, during which no ions are accumulated.

For a certain analytical task, first a required mobility resolution to solve the analytical task has to be chosen, e.g. $R_{mob}\approx 80$. This mobility resolution determines the scan time. With optimum gas pressure and gas speed, the scan time $t_s$ to achieve this resolution over a wide range of mobilities amounts to about 60 milliseconds. A simple calculation shows, that for a utilization rate of 80 percent of the ions from the ion source, the accumulation time $t_a$ must be in the range of 200 milliseconds. Experience shows, however, that with usual high gain electro spray ion sources, ions get lost in the tube-like tunnel (11) at accumulation times above 40 milliseconds, resulting in a duty cycle of only 40 percent. And it is mainly the most interestingly high mass ions which get lost.

There is still a need for devices and methods operating with highest utilization rates (duty cycle) of the ions generated in an ion source of a mass spectrometer, thereby reducing the restriction of the mobility resolution, in particular with an electrospray ion source coupled to liquid chromatography for analyzing complex samples in the field of bottom-up proteomics.

SUMMARY OF THE INVENTION

The invention provides an ion mobility analyzer that comprises an RF field for radially confining ions along an axis, a region with an axial electric DC field and a gas flow along the axis counteracting the electric DC field in the region. The region comprises a rising edge with an increasing axial electric DC field or a falling edge with a decreasing axial electric DC field and the slope of the electric field strength along the axis is not constant at a substantial portion of the edge.

The slope of the electric field strength along the axis is preferably not constant at more than 30%, more preferably at more than 50% and most preferably at more than 75% of the edge. The RF field is preferably quadrupolar and the gas flow can be radially confined in a tube along the region.

The region preferably comprises a rising edge and a downstream plateau with a substantially constant axial electric DC field such that an electric DC field barrier is formed against which ions are driven by the gas flow after being introduced into the ion mobility analyzer. The slope of the rising edge near the plateau can be lower than the slope in other parts of the rising edge. The slope preferably decreases monotonically along the rising edge towards the plateau. At the rising edge, the electric field strength along the axis can increase proportionally to $(z-z_o)^p$ at the rising edge of the field barrier, with z being the coordinate along the axis, $z_o$ being an offset and exponent p being lower than one. The exponent p has preferably a value in the range $0.3 \le p \le 0.9$. The exponent p has most preferably a value $p=\frac{2}{3}$ or $p=\frac{1}{2}$.

The region can also comprise a falling edge and a downstream plateau with a substantially constant axial electric DC field and wherein the gas flow blows ions against the falling edge such that the ions are hindered to pass the falling edge. Preferably, the slope is monotonically increasing along the falling edge towards the plateau.

The ion mobility analyzer can comprise electrodes which are arranged in the region along the axis and supplied with electric DC potentials such that the electric field strength at the rising or falling edge is piecewise linear wherein the slopes of the electric field strength differ in at least two piecewise portions of the edge. The slopes in the piecewise portions are preferably adjusted depending on the effective radially confining potential which acts on ions of the ion species trapped in the portions. The effective radially confining potential depends on the amplitude and frequency of the quadrupolar RF field, on the mass, cross section, and charge of the ions and in particular on the space charge of the ion species trapped in the portions. The slope is reduced at trapping positions with high space charge in order to reduce radial defocussing due to space charge of the ion species. Multiple digital-to-analog converters (DAC) can generate multiple DC potentials which are applied to the electrodes arranged in the region along the axis such that the slope of electric field along the edge (rising or falling) can freely be adjusted.

The ion mobility analyzer comprises one of means for adjusting the speed of the gas velocity in the region and the means for adjusting the field strength at the plateau.

The invention further comprises a method for mobility analyzing ions, comprising following the steps of:
  providing an RF field for radially confining the ions along an axis;
  providing an axial electric DC field that comprises a rising edge with an increasing electric field strength or a falling edge with a decreasing electric field strength and additionally a downstream plateau with a substantially constant electric field strength;
  providing a gas flow which drives ions against the axial electric DC field such that ions of at least two ion species are substantially trapped at the edge;
  adjusting the slope of the axial electric DC field at the trapping positions of the at least two ion species such that the slope at the respective trapping position of the ion species at the edge is different; and
  accumulating and trapping ions in the ion mobility analyzer and scanning the field strength at the plateau.

The method can further comprise determining the ion density as a function of mobility or even as a two-dimensional function of mass and mobility, adjusting the slope of the axial electric DC field along the edge to minimize radial ion losses due to space charge repulsion of the ion species at the respective trapping positions, and rescanning the field strength at the plateau after an additional accumulation and trapping step. The ions are preferably detected by a mass analyzer downstream of the axial electric DC field such that the ion density is determined as a two-dimensional distribution with a mobility axis and a mass axis. The ion density as a function of mobility can be determined from the two-dimensional distribution by integration along the mass axis. The slope at a trapping position of an ion species can also be adjusted in time during the accumulation and trapping of the ions in the ion mobility analyzer.

The invention further provides a system that comprises a mass analyzer and an ion mobility analyzer wherein the ion mobility analyzer comprises an RF field for radially confining ions along an axis, a region with an axial electric DC field and a gas flow along the axis counteracting the electric DC field in the region. The region comprises a rising edge with an increasing axial electric DC field or a falling edge with a decreasing axial electric DC field. The slope of the electric field strength along the axis is not constant at a substantial portion of the edge. The mass analyzer can be one of an orthogonal time-of-flight mass analyzer, a quadrupole filter, an RF ion trap, an electrostatic ion trap and an ion cyclotron resonance mass spectrometer and is located downstream of the ion mobility analyzer. The system can further comprise a fragmentation cell located between the ion mobility analyzer and the mass analyzer. A preferred system comprises an upstream mobility analyzer, a quadrupole mass filter, a fragmentation cell and a downstream high performance mass analyzer, e.g. an orthogonal time-of-flight mass analyzer, an electrostatic ion trap and an ion cyclotron resonance mass spectrometer.

The present invention can preferably be applied in the field of bottom-up proteomics where a liquid chromatography separation is coupled to a tandem mass spectrometer with an electro-spray ion source, in particular to a tandem mass spectrometer comprising a quadrupole mass filter and a downstream high performance mass analyzer.

BRIEF DESCRIPTION OF THE DRAWINGS

FIG. 1 schematically illustrates the ion mobility spectrometer according to the state of the art, as described in U.S. Pat. No. 7,838,826 B1 (M. A. Park, 2008). In the bottom part, the principal set-up with an entrance funnel (10), presenting open space between the apertures to let escape a part of the gas flow, a closed tube-like tunnel (11), and an open exit funnel (12) is shown. The tunnel represents the essential part of the mobility spectrometer. A laminar gas flow (14) inside the tube-like tunnel (11) reaches a parabolic velocity distribution, driving the ions through the tube-like tunnel (11). A quadrupolar RF field inside the tube-like tunnel (11) keeps the ions essentially in the axis of the device and an electric DC field barrier (not shown) separates the ions according to their mobilities. In the upper part of FIG. 1, two diaphragm electrodes of the device are presented, one belonging to the entrance funnel (10), and one to the tube-like tunnel (11), both segmented into quadrants (15, 16) and (17, 18) respectively. By the segmentation into quadrants, an RF voltage can produce the quadrupolar RF field (19) inside the devices.

FIG. 2 shows the operation of the device shown in FIG. 1. Ions from an electrospray ion source (not shown) are introduced, entrained by a gas (7) via a capillary (8) into the first chamber of a vacuum system. A repelling DC potential applied to the repeller plate (9) drives the ions (6) into the entrance funnel (10). A laminar gas flow with parabolic velocity profile (14) drives the ions through the tube-like tunnel (11) and against the electric field barrier. In the bottom part of FIG. 2, three phases of the electric field profile E(z) along the z axis are shown, generated by DC voltage applied between locations (20) and (24) and divided by precision resistors along the diaphragms (not shown). The electric field profile has a linearly increasing electric DC field at the rising edge between locations (20) and (23), and a plateau with constant electric DC field between (23) and (24). The gas flow is symbolized by arrows (16). In a first "accumulation phase" (A), the ions are accumulated on the rising edge of the electric DC field, where ions of low mobility (mainly heavy ions of large collision cross section) collect in the high electric field near the upper end of the rising edge, whereas ions of high mobility gather in the low electric field near the foot of the rising edge, as indicated by the size of the dots symbolizing the ions. In a second phase (B), the "trap phase", the supply of ions is stopped by an attracting voltage at the repeller plate (9), and the ions finally assume their equilibrium locations on the rising edge. In a third phase (C), the "scan phase", the supply voltage for the electric DC field barrier is steadily decreased, and ions of increasing mobility can escape towards an ion detector, particularly to a mass spectrometer operating as ion detector.

DETAILED DESCRIPTION

The present invention relates to trapping ion mobility spectrometers as described in document U.S. Pat. No. 7,838,826 B1 (M. A. Park, 2008) and provides apparatus and methods to increase the utilization rate of ions produced in an ion source. In a trapping ion mobility spectrometer, ions are commonly driven by the gas flow against an electric DC field barrier and are stopped there because they cannot surmount the electric DC field barrier. The original instrument was built with a linearly increasing electric field at the front of the barrier, corresponding to a quadratic increase of the electric potential. In equilibrium, ions with high mobility (small cross section) gather near the foot of the barrier, ions with low mobility gather (large cross section) near the summit.

The present invention is based on the recognition that with long accumulation times, the high mass ions (low mobilities) get lost because they are much less strongly focused by the pseudo-potential within the quadrupolar RF field than low mass ions (high mobility). The effective force of the pseudo-potential is proportional to $z^2/m$, with z being the number of charges and m being the ion mass. High mass ions are less strongly focused and, therefore, more strongly influenced by a Coulomb repulsion due to their space charge. Multiply charged ions are more strongly focused, but also strongly repelled by Coulomb forces.

It is an idea of the invention to decrease the density of the ions with low mobility near the summit by decreasing the field gradient there, and to accept a higher density of high mobility ions near the foot of the electric DC field barrier by a steeper field gradient. High mobility ions are much more strongly focused by the pseudo-potential and are much less influenced by space charge repulsion. This goal can be achieved by non-constant field gradients of the electric field E(z) at the front of the barrier, e.g. by an electrical field ramp $E \sim z^p$, with an exponent p smaller than p=1.0, and z being the coordinate along the axis of the device. This decreases the field gradient near the summit, uncompressing the high mass ion density, and increases the field gradient near the foot, compressing the low mass ion density. A favorable range for the exponent p is 0.3<p<0.9; favorable values are p=⅔, or p=½.

Furthermore, the length of rising edge of the electric DC field barrier can be enhanced to several centimeters, preferably to more than three centimeters, more preferably to more than six centimeters and up to ten centimeters or even more, uncompressing all ions along the field ramp.

Experiments with known mixtures of ions, using a standard high performance electrospray ion source, have shown that the accumulation time could be increased from about 40 milliseconds to more than 200 milliseconds with about the same low loss of high mass ions. The duty cycle could be increased by these measures from about 40% up to 80% and higher.

As mentioned above, the present invention is partly based on the ion mobility spectrometer as described in document U.S. Pat. No. 7,838,826 B1 (M. A. Park, 2008) and schematically illustrated in FIG. 1. The invention provides embodiments for apparatus and methods to increase the utilization rate of the ions from the ion source ("duty cyle").

The original instrument was built with an electric field linearly increasing at the rising edge of the field barrier, as shown in the bottom part of FIG. 2. During the accumulation phase (A), ions with high mobility (small cross section) gather near the foot of the electric DC field barrier, ions with low mobility (large cross section) gather near the summit. In a short trap phase (B) of only about two milliseconds, where a further supply of ions is barred, the ions reach their equilibrium locations along the z-axis. If the ions have evenly distributed mobilities, they appear evenly distributed along the z-axis, as indicated by the dots in the figure. In the scan phase (C), the complete profile of the electric field is steadily decreased, and ions of increasing mobilities can leave mobility-separated the spectrometer towards detection, e.g. by a mass spectrometer.

The measured ion current curve presents directly the ion mobility spectrum from low ion mobilities to high ion mobilities. The device is denominated "TIMS", "trapped ion mobility spectrometer". If a mass spectrometer is used as the ion detector, the total ion current represents the mobility spectrum, but additionally, the mass of the ions can be determined resulting in a two-dimensional ion distribution along a mass axis and a mobility axis.

Figure 3:
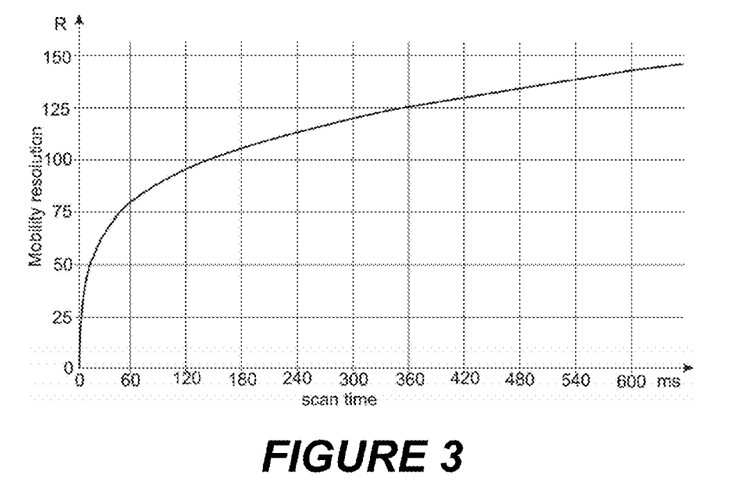
FIG. 3 shows the dependence of the mobility resolution R, given for ions of low mobility ($K\approx0.5$ $cm^2/Vs$), on the scan time $t_s$. The scan time $t_s$ comprises the full scan from low mobilities ($K\approx0.5$ $cm^2/Vs$) to high mobilities ($K\approx1.0$ $cm^2/Vs$). At a scan time of 60 milliseconds over the full range of mobilities, a mobility resolution R of about 80 is achieved; a mobility resolution of $R\approx125$ needs a scan time of 360 milliseconds.

The mobility resolution of this spectrometer depends strongly on the scan time $t_s$, needed to scan the usual mobility range from low mobilities (K≈0.5 cm²/Vs) to high mobilities (K≈1.0 cm²/Vs). The dependence is shown in FIG. 3. Since the mobility resolution $R_{mob}$ is slightly dependent on the mobility K itself, the dependence is shown for ions with K≈0.5 cm²/Vs.

Figure 4:
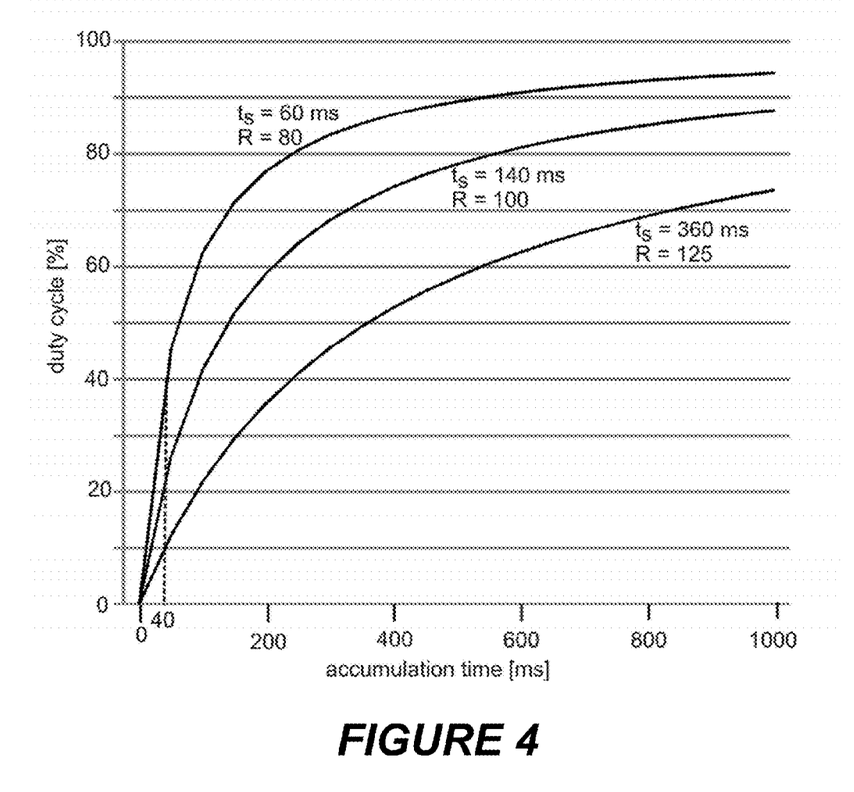
FIG. 4 shows the dependence of the duty cycle on the achievable accumulation time, for three different scan times: $t_s$=60 ms, 140 ms and 360 ms, resulting in mobility resolutions R of 80, 100, and 125 respectively.

The utilization rate of ions produced in an ion source, accumulated, and subsequently analyzed in an analyzer, is determined by the ratio $q=t_a/(t_a+t_s)$ wherein $t_a$ is the ion accumulation time and $t_s$ the measuring scan time, during which no ions are accumulated. The trap time can usually be neglected because it is very short. The utilization rate is also called "duty cycle". In FIG. 4, the dependence of the duty cycle on the accumulation time is outlined for three different scan times $t_s$ (corresponding to three different mobility resolutions R). The longer the accumulation time $t_a$, the higher the utilization rate q, provided that no ions get lost during accumulation, and all ions can be measured by the analyzer without ion losses or saturation effects.

The invention is based on the recognition that with long accumulation times, the high mass ions, usually having low mobilities because of their high cross sections, get lost first because they are less strongly focused in a radial direction by the pseudo-potential within the quadrupolar RF field than low mass ions, showing high mobility. The effective force of the pseudo-potential is proportional to $z^2/m$, with z being the number of charges and m being the ion mass. High mass ions are only weakly focused by the pseudo-potential, and thus are more sensitive to space charge repulsion, driving the ions radially out of the device. With standard high performance electrospray ion sources, severe losses of high mass ions already start with accumulation times above 40 milliseconds and, for complex samples, with even lower accumulation times. If a scan time $t_s$ of 60 milliseconds was selected to achieve a mobility resolution of $R_{mob}\approx 80$ for the most interesting low mobility ions, the utility rate q only amounts to only 40% if an accumulation time of 40 milliseconds is applied. If a higher mobility resolution should be achieved, e.g. $R_{mob}\approx 110$, the scan time must be adjusted to about 120 milliseconds, and the utilization of ions falls to 25%.

Figure 5:
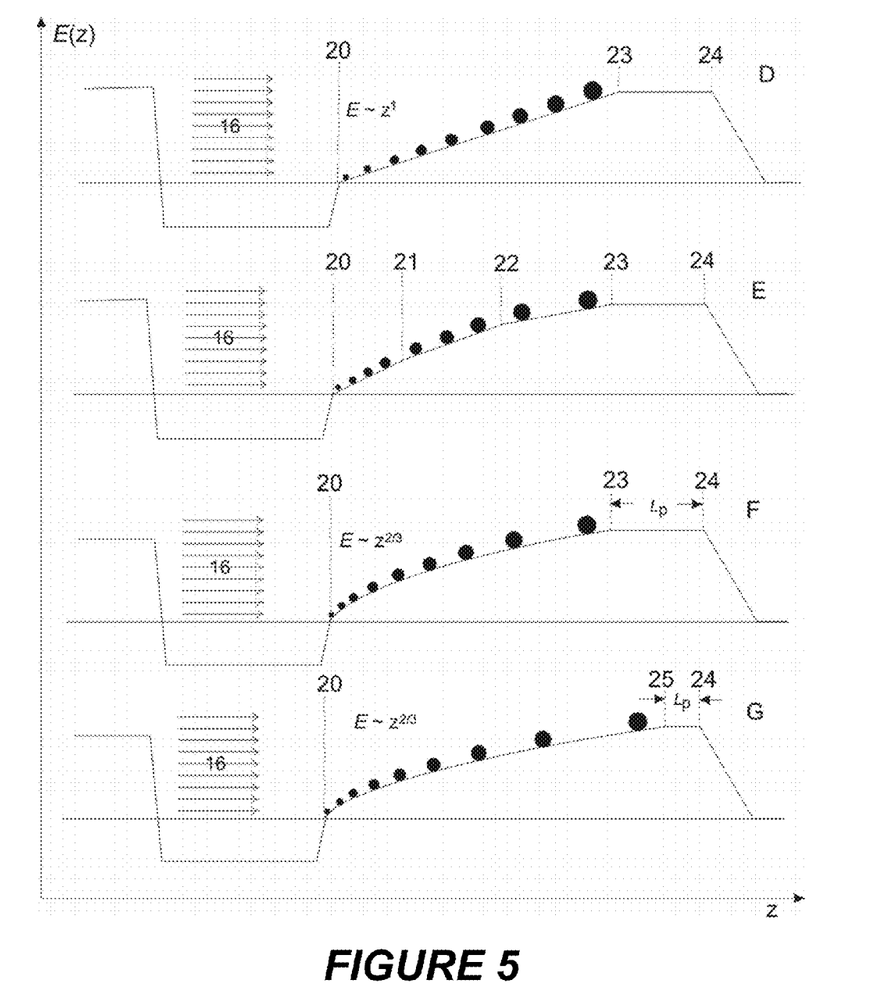
FIG. 5 shows four different spatial profiles of the electric field; the lower three profiles symbolically show the effect of the invention on the density of ions of different cross section, as indicated by dots of different diameters. In the upper part (D), the electric field strength increases linearly along the axis z of the device, as originally described in the document cited above, showing equal ion density along the rising edge. Below, in part (E), the rising edge of the electric field shows three portions with piecewise linear electric fields with different slopes, between z locations (20) and (21), (21) and (22), and (22) and (23) respectively, the lowest slope near the top. Near the top, ion density and space charge are diminished, compared with the profile in part (D) at the top. In the third profile (F), the electric field increases proportionally to $z^{2/3}$. As indicated by the dots, high mass ions near the top of the rising edge are uncompressed by the field proportional to $z^{2/3}$, whereas low mass ions are compressed at the foot of the rising edge. Near the top of the ramp, the space charge is diminished, and losses of high mass ions are considerably reduced. In the bottom part (G), a further decompression of ions is achieved by a shorter length $L_p$ of the plateau.

It is an idea of the invention, to decrease the density for low mobility ions near the summit, and to accept a higher density of high mobility ions near the foot of the electric DC field barrier. This goal can be achieved by a non-constant gradient (slope) of the electric field E(z) at the front of the electric DC field barrier. For example, an embodiment of the invention is given by the profile in part (E) of FIG. 5, showing a piecewise linear increase with three different gradients of the electric field. The electric field gradient between z positions (20) and (21) is steepest, the gradient between (21) and (22) is medium, and between (22) and (23) is flattest. The flat gradient near the top is uncompressing the ions with low mobility, reducing the space charge repulsion. Of course, more than only three gradients may be applied.

Another embodiment of the invention is shown in part (F) of FIG. 5. Here, the electric field increases non-linearly according by the function $E(z) \sim z^p$, with an exponent $p=\frac{2}{3}$ and z being the position along the z-axis. This electric field at the rising edge results in a decreased field gradient near the summit, uncompressing the high mass ion density, and increases the field gradient near the foot, compressing the low mass ion density. The value $p=\frac{2}{3}$ is only an example; in fact, the exponent p is preferably smaller than 1.0. A preferable range for the exponent p is $0.3 \le p \le 0.9$. If the mixture of ions contains many high mass ions, a value of $p=\frac{1}{2}$ may be more favorable; in the extreme, even $p=\frac{1}{3}$ may serve the purpose best. For other mixtures of ions or specific problems or applications it might be favorable to decrease the electric field gradient at other parts of the edge, e.g. in the middle of the edge.

For reason of comparison, the upper part (D) of FIG. 5 presents a linearly increasing electric field at the rising edge, where it is to be seen that ions of an evenly occupied range of mobilities are evenly distributed along the rising edge. In practice, however, the mobilities of ions are rarely evenly distributed.

Experiments with known mixtures of ions, using a standard high performance electrospray ion source and a mixture of ions with a wide distribution of mobilities, have shown that the accumulation time could be increased from 40 milliseconds to about 200 milliseconds, using a ramp with an field E(z) increasing proportional to $z^{2/3}$, without significant loss of high mass ions. For scan times of 60 milliseconds ($R\approx 80$), the duty cycle could be increased by these measures from about 40% up to 80%.

Furthermore, the rising edge of the electric DC field barrier can be made as long as possible, e.g. up to five centimeters or more, uncompressing all ions along the field ramp. The bottom part (G) of FIG. 5 schematically presents the combined effect of a decreased length $L_p$ of the plateau, and the elongated rising edge proportional to $z^{2/3}$. With this additional uncompressing effect of a short plateau, the accumulation time could be increased to about 300 milliseconds without substantial losses of high mass ions. Experiments as well as theory reveal that the mobility resolution does not suffer substantially by a shortened plateau.

It is a further idea of the invention, to use a variable (spatially adjustable) electric field profile and, in particular, to vary the profile as the result of one or more preceding measurements of the ion density along the mobility axis of the mobility spectrum. As an example for an embodiment with variable field profile, the stepwise linear increase can be varied, as shown in part (E) of FIG. 5, by a voltage generator delivering three voltages $V_{21}$, $V_{22}$ and $V_{24}$, applied to positions (21), (22) and (24). By adjusting the voltages $V_{21}$ and $V_{22}$ relative to voltage $V_{24}$, a variety of field profiles can be generated. If a preceding measurement shows a high density of low mobility ions, the field gradient between positions (22) and (23) can, for example, be made as flat as necessary to avoid losses. As a matter of course, more adjustable voltages may be used at more z positions.

With a more complex device, the voltages at all or a large part of the diaphragms along the z axis may be generated by a series of digital-to-analog converters (DAC). Then one can generate any field profile, enabling an operation which can respond exactly to any distribution of ions on the mobility scale.

The various embodiments of the TIMS-MS devices can serve different analytical tasks. As an example, an analytical task may require a mobility resolution of $R\approx 120$, needing a scan time of about 300 milliseconds over the range of mobilities from $K\approx 0.5$-$1.0$ cm²/Vs. This task can be solved with a rising edge according to part (G) in FIG. 5. If the accumulation time is set to 300 milliseconds, a utilization rate of fifty percent of ions delivered from the ion source can be achieved. This duty cycle, however, can only be achieved without major losses of high mass ions when the gradient of the electrical field is reduced near the top of the electric DC field barrier according to this invention.

In case that the accumulation and scan time are both set to 300 milliseconds, about five scans can be performed in a period of three seconds. With a modern time-of-flight mass spectrometer having an acquisition rate of 10 kilosamples per second, about 3000 mass spectra can be acquired in each 300 millisecond scan, resulting in about 30000 mass spectra per period of three seconds. If the mobility axis is divided into 120 segments, and in each of the segments the corresponding mass spectra with ions of equal mobility are added, in each segment 250 mass spectra per three second period are collected. A period of three seconds is a favorable time period to sample the ions from a liquid chromatograph (HPLC), coupled to a mass spectrometer, delivering substance peaks of about 20 to 30 seconds in length, This operation delivers mass spectra with high quality for ions efficiently separated by their mobility.

The invention proposes a preferred ion mobility spectrometer, in which the ions are kept near the axis z of a tube by a radially acting quadrupolar RF field, and a gas flow through the tube blows the ions against an electric DC field barrier, wherein an electric field strength E(z) along the axis z of the device which has a non-constant field gradient (slope) at the rising edge of the barrier, whereby the field gradient near the top of the electric DC field barrier is lower than the field gradients in other parts of the rising edge.

In one embodiment, the electric field strength E(z) along the axis z of the device increases proportionally to $z^p$ at the rising edge of the field barrier, with exponent p being lower than 1.0. The exponent p may have a value in the range $0.3<p<0.9$; distinct values are $p=\frac{2}{3}$ or $p=\frac{1}{2}$.

In another embodiment, a voltage generator delivers several voltages to adjust the profile of the electric field strength E(z) at the rising edge of the electric DC field barrier along the axis z of the device. A control unit may use data of the ion density, measured as a function of the mobility in one or more preceding scans, to control the profile of the electric field strength E(z) along the z-axis of the device to minimize ion losses during accumulation. During the mobility scan phase the profile of the electric field might be changed in a way that the gradient of the electric field strength does not exceed the gradient at which the ions are accumulated.

Figure 6:
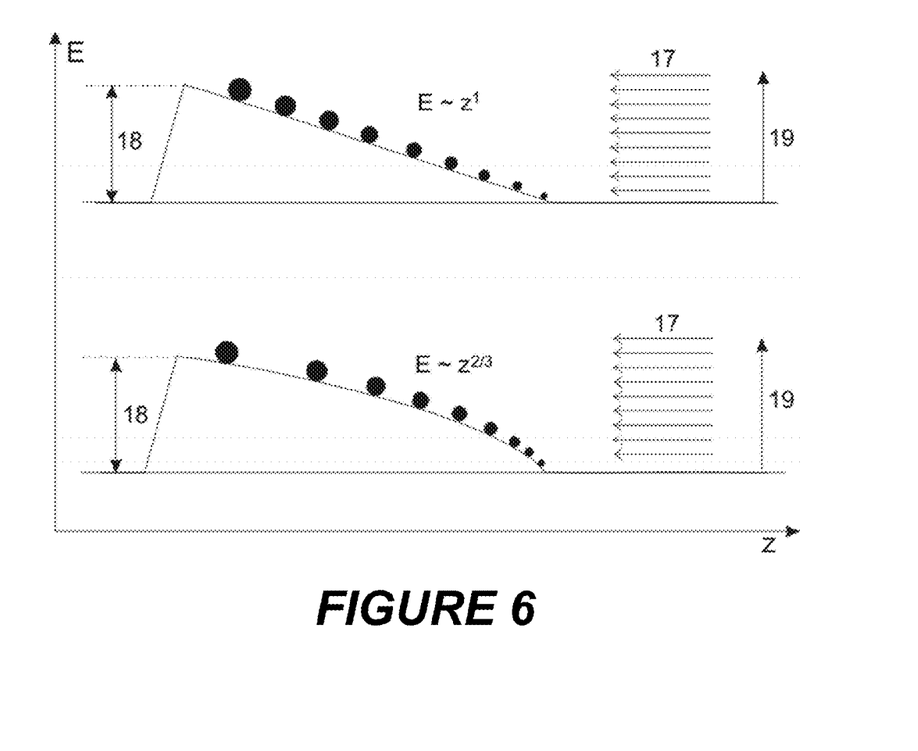
FIG. 6 shows another mobility spectrometer which operates with a gas flow (17) driving ions against a falling edge. When ions enter the device from the ion source (coming from the left side), the ions gather at the falling edge of the electric field profile and are separated by their mobility, as indicated by the size of the dots. Changing the electric field profile, as indicated by arrow (19), allows the ions, starting with ions of high mobility, to escape through the gas flow in the direction of the ion detector, resulting in a mobility spectrum. Also here, as shown in the bottom part of the figure, a curved falling edge helps to lower the space charge effect for heavy ions of low mobility, and to save those ions from disappearing in a radial direction.

In another embodiment of the trapping ion mobility spectrometer shown in FIG. 6, the gas flow is reversed compared to the embodiment show in FIG. 5 and drives the ions against the electric field of a falling edge. When the entrance field allows the ions from the source (coming from the left side) to enter the device, ions are trapped at the falling edge of the electric field profile and are spatially separated by their mobility, as indicated by the size of the dots. Changing the electric field profile, as indicated by arrow (19), allows ions, starting with ions of high mobility, to be driven by the steadily increasing electric field against the counter-acting gas flow (17) towards the ion detector, resulting in a mobility spectrum. As shown in the bottom part of the FIG. 6, a curved falling edge with non-constant slope of the electric field strength helps to lower the space charge effect for heavy ions of low mobility, and to save those ions from disappearing in lateral direction.

The invention furthermore proposes a method to operate an ion mobility spectrometer, in which the ions are kept near the axis z of a tube by a radially acting quadrupolar RF field, and a gas flow through the tube blows the ions against an electric DC field barrier, wherein the ion density is measured as a function of the mobility in one or more preceding scans, and the profile of the electric field strength E(z) along the axis z of the device is adjusted to minimize ion losses during accumulation.

The invention claimed is:

1. An ion mobility analyzer comprising an RF field for radially confining ions along an axis, a region with an axial electric DC field and a gas flow along the axis counteracting the electric DC field in the region, wherein the region comprises a rising edge with an increasing axial electric DC field or a falling edge with a decreasing axial electric DC field, characterized in that the slope of the electric field strength along the axis is not constant at a substantial portion of the edge.

2. The ion mobility analyzer according to claim 1, wherein the region comprises a rising edge and a downstream plateau with a substantially constant axial electric DC field such that an electric DC field barrier is formed against which ions are driven by the gas flow after being introduced into the ion mobility analyzer.

3. The ion mobility analyzer according to claim 2, wherein the slope of the rising edge near the plateau is lower than the slope in other parts of the rising edge.

4. The ion mobility analyzer according to claim 3, wherein the slope is monotonically decreasing along the rising edge towards the plateau.

5. The ion mobility analyzer according to claim 4, wherein the electric field strength along the axis increases proportionally to $(z-z_o)^p$ on the rising edge of the field barrier, with z being the coordinate along the axis, $z_o$ being an offset and exponent p being lower than one.

6. The ion mobility analyzer according to claim 5, wherein the exponent p has a value in the range $0.3 \leq p \leq 0.9$.

7. The ion mobility analyzer according to claim 6, wherein the exponent p has a value $p=\frac{2}{3}$ or $p=\frac{1}{2}$.

8. The ion mobility analyzer according to claim 1, wherein the region comprises a falling edge and a downstream plateau with a substantially constant axial electric DC field and wherein the gas flow blows ions against the falling edge such that the ions are hindered to pass the falling edge.

9. The ion mobility analyzer according to claim 8, wherein the slope is monotonically increasing along the falling edge towards the plateau.

10. The ion mobility analyzer according to claim 1, wherein the ion mobility analyzer comprises electrodes which are arranged in the region along the axis and supplied with electric DC potentials such that the electric field strength on the edge is piecewise linear wherein the slopes of the electric field strength differ in at least two piecewise portions of the edge.

11. The ion mobility analyzer according to claim 10, wherein the slopes in the piecewise portions are adjusted depending on the effective radially confining potential which acts on ions of the ion species trapped in the portions.

12. The ion mobility analyzer according to claim 11, wherein the effective radially confining potential depends on the amplitude and frequency of the quadrupolar RF field, on the mass and charge of the ions and on the space charge of the ion species trapped in the portions.

13. The ion mobility analyzer according to claim 1, wherein the RF field is quadrupolar.

14. The ion mobility analyzer according to claim 1, wherein the gas flow is radially confined in a tube along the region.

15. The ion mobility analyzer according to claim 2, wherein the ion mobility analyzer comprises one of means for adjusting the speed of the gas velocity in the region and means for adjusting the field strength at the plateau.

16. A method for mobility analyzing ions, comprising the steps of:
  providing an RF field for radially confining the ions along an axis;
  providing an axial electric DC field comprising a rising edge with an increasing electric field strength or a falling edge with a decreasing electric field strength and a downstream plateau with a substantially constant electric field strength;
  providing a gas flow which drives ions against the axial electric DC field such that ions of at least two ion species are substantially trapped on the edge;
  adjusting the slope of the axial electric DC field at the trapping positions of the at least two ion species such that the slope at the respective trapping position of the ion species at the edge is different; and
  accumulating and trapping ions in the ion mobility analyzer and scanning the field strength at the plateau.

17. The method according to claim 16, further comprising the steps of:
- determining the ion density as a function of mobility or as a two-dimensional function of mass and mobility,
- adjusting the slope of the axial electric DC field along the edge to minimize radial ion losses due to space charge repulsion of the ion species at the respective trapping positions; and
- rescanning the field strength at the plateau after an additional accumulating and trapping step.

18. A system comprising a mass analyzer and an ion mobility analyzer wherein the ion mobility analyzer comprises an RF field for radially confining ions along an axis, a region with an axial electric DC field and a gas flow along the axis counteracting the electric DC field in the region, said region comprises a rising edge with an increasing axial electric DC field or a falling edge with a decreasing axial electric DC field, and wherein the slope of the electric field strength along the axis is not constant at a substantial portion of the edge.

19. The system according to claim 18, wherein the mass analyzer is one of an orthogonal time-of-flight mass analyzer, a quadrupole filter, an RF ion trap, an electrostatic ion trap and an ion cyclotron resonance mass spectrometer and is located downstream of the ion mobility analyzer.

20. The system according to claim 19, wherein the system further comprises a fragmentation cell located between the ion mobility analyzer and the mass analyzer.

* * * * *